United States Patent [19]

Wolfe et al.

[11] Patent Number: 4,999,298
[45] Date of Patent: Mar. 12, 1991

[54] HOLLOW FIBER BIOREACTOR CULTURE SYSTEM AND METHOD

[75] Inventors: Richard A. Wolfe, Ellisville, Mo.; Aaron H. Heifetz, Columbia; James A. Braatz, Beltsville, both of Md.; David M. Donofrio, Rockport, Mass.

[73] Assignee: W. R. Grace & Co.-Conn., Lexington, Mass.

[21] Appl. No.: 186,609

[22] Filed: Apr. 27, 1988

[51] Int. Cl.⁵ .......................... C12N 5/00; C12N 3/06
[52] U.S. Cl. .................................. 435/240.242; 435/3; 435/289; 435/813
[58] Field of Search ..................... 435/3, 240.242, 289, 435/813; 210/743, 196

[56] References Cited

U.S. PATENT DOCUMENTS

| | | | |
|---|---|---|---|
| 3,883,393 | 5/1975 | Knazek et al. | 195/1.8 |
| 3,997,396 | 12/1976 | Delente | 195/1.8 |
| 4,220,725 | 9/1980 | Knazek et al. | 435/285 |
| 4,225,671 | 9/1980 | Puchinger et al. | 435/71 |

FOREIGN PATENT DOCUMENTS 8602378 4/1986 PCT Int'l Appl.
8706610 11/1987 PCT Int'l Appl.

OTHER PUBLICATIONS

"Disinfection, Sterilization, and Preservation", 3d ed., Seymour S. Block (1983), pp. 133 & 135.
"Perry's Chemical Engineer's Handbook", 6th ed., Perry, R. H. and Green, D. W. (1984), pp. 6-62.
"Hollow Fiber Cell Culture", W. R. Grace & Co., Publication No. 535, Jan. 1986.

Primary Examiner—Robert J. Warden
Assistant Examiner—Jeffrey R. Snay
Attorney, Agent, or Firm—Stacey L. Channing; William L. Baker

[57] ABSTRACT

The cell culturing system of the present invention includes a tubular membrane, e.g. hollow fiber, cartridge. Provision is made for the continuous circulation of a nutrient-containing medium through the tube side of the cartridge by pumping the nutrient-containing medium in an endless loop. The cells to be cultured are placed within the cartridge on the shell side where the desired extracellular products are accumulated. Nutrients are assimilated into the cell culture through the semipermeable tubular membranes and waste products are removed by passing through the semipermeable membranes into the recirculating nutrient-containing medium. Within the endless loop are located a circulating pump, an oxygenator and a pH probe. The system additionally includes a variable delivery feed pump for continuously injecting fresh nutrient-containing solution into the loop, which feed pump is operated at a rate responsive to the measured pH. A portion of the stream exiting the cartridge is continuously split off at a rate identical to that for the introduction for fresh nutrient-containing solution in order to maintain cellular waste products at a suitably low level. The conventional nutrient-solution preparation reservoir has been eliminated from the loop in order to simplify the system and reduce the potential points of entry for contaminating microorganisms. The membrane cartridge is mounted with its longitudinal axis at approximately 60° with respect to the horizontal.

16 Claims, 1 Drawing Sheet

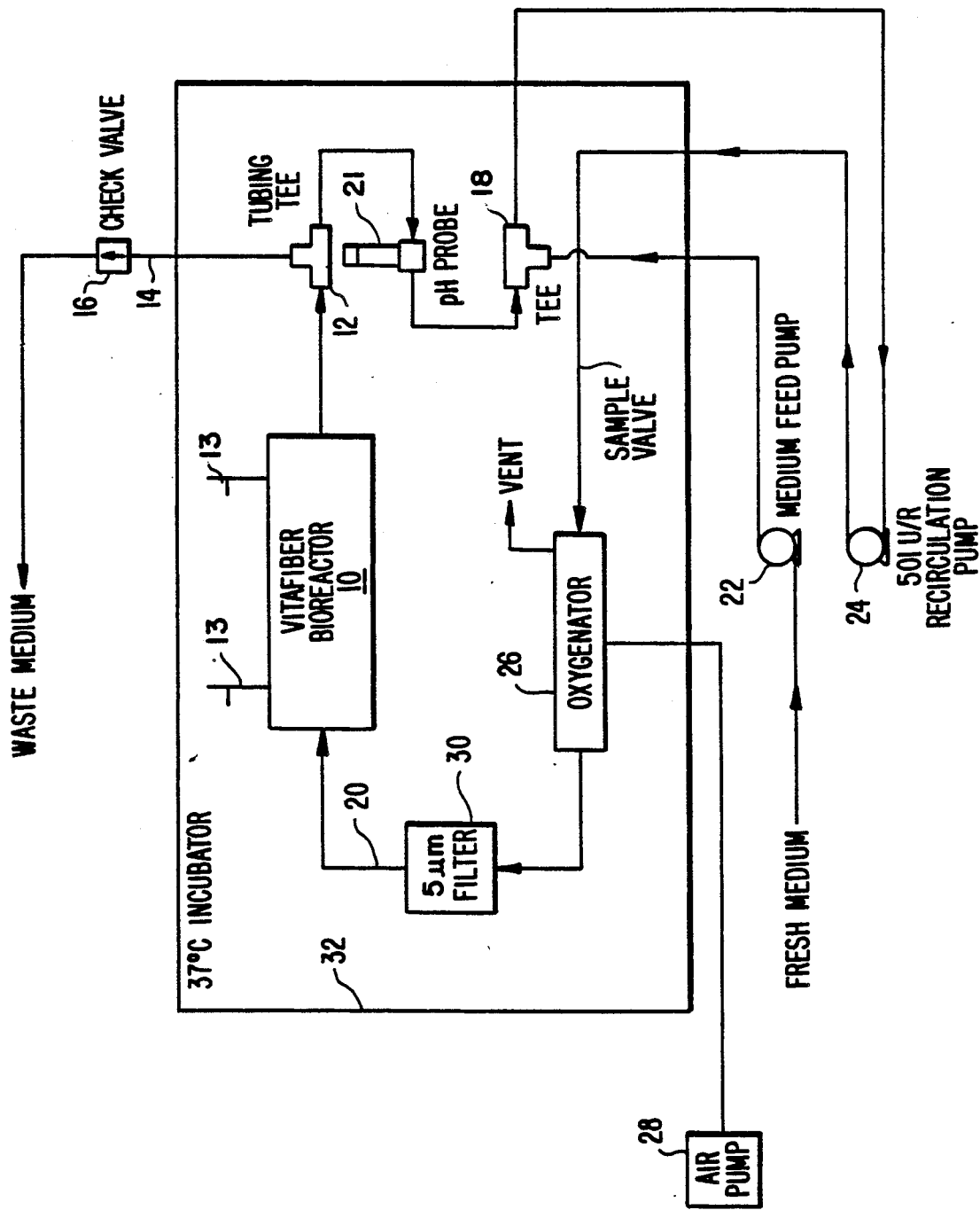

HOLLOW FIBER BIOREACTOR CULTURE SYSTEM AND METHOD

BACKGROUND OF THE INVENTION

The present invention relates to apparatus and method of growing cells in vitro, particularly mammalian cells.

U.S. Pat. No. 3,883,393 and U.S. Pat. No. 4,220,725, both issued to Knazek et al, describe apparatus and methods for maintaining and growing mammalian cells in vitro. The apparatus disclosed by Knazek et al includes a cartridge of semipermeable tubular members, more specifically, semipermeable hollow fibers. In the methods disclosed by Knazek et al, cells suspended in a nutrient medium are introduced into the shell side of the bioreactor and allowed to settle on the hollow fibers which they refer to as "capillaries." A nutrient medium is continuously circulated through the tube side of the bioreactor to nourish the cells contained therein and thereby promote growth. The waste products of the growing cells were allowed to accumulate within the recirculating "perfusion medium" and that "perfusion medium" was disposed of and replaced by fresh nutrient medium everyday or every other day. The changing of the nutrient medium was necessary in order to prevent substances toxic to the cells, e.g. lactate, from reaching a level which would kill or deplete the cell culture. Knazek et al included a stirred reservoir or hold tank within their loop as a convenient method for adding and withdrawing the liquid nutrient medium on alternating days or on a daily basis. Accordingly, Knazek et al adopted the conventional approach to the culturing of mammalian cells which is essentially a batch process with respect to the replacement of the nutrient medium.

"VITAFIBER ® II/Plus" is considered an improvement over the apparatus and method of Knazek et al in that it enables operation with replenishment of the nutrient liquid on a continuous basis, rather than in a batch manner. Nutrient and waste levels in the recirculating liquid medium can be better controlled. This enhanced controlability is particularly important in the culturing of cells which are very sensitive with respect to lactate levels. Provision is made for automatic pH control by addition of acid or base. However, no provision is made for automatic control of nutrients and the system is subject to nutrient depletion.

In these prior art systems, lactate level was monitored by addition of a pH color indicator, e.g. phenol red, to the liquid medium. It has also been conventional in this art to monitor lactate levels by periodically withdrawing samples from the liquid medium and analyzing for lactate using a conventional lactate analyzer

SUMMARY OF THE INVENTION

A continuing problem associated with prior art techniques for culturing mammalian and other cell lines is the ever-present danger of contamination or destruction of the cell culture by another microorganism. The present inventors have found that the seal or bearing surrounding the stirrer in the reservoirs of the prior art apparatus discussed above has been an entry point for foreign microorganisms in the past. Also, the stirring per se came to be regarded as a cause of protein denaturation. Applicants have discovered that they can obtain sufficient mixing of fresh nutrient solution by injecting the fresh solution into the recirculating loop of liquid medium. Thus, the present invention dispenses with the need for a stirred reservoir or holding tank and thereby eliminates a potential point of entry enhanced controlability is particularly important in the for contaminating microorganisms. Further, by operation under an elevated pressure the present invention offers further protection against entry of a contaminating microorganism.

Applicants have also discovered that an optimum nutrient level may be maintained with maximum efficiency by providing for control of the pump feeding fresh nutrient solution into the medium recirculation loop, responsive to the pH of the liquid medium within the recirculation loop, as measured by a enhanced controlability is particularly important in the conventional pH probe. In the present system the fresh nutrient solution is added at a constant pH, e.g. 7.3 or 7.4. Thus, in the present system, unlike the prior art a drop in pH compensated for by an increase in the amount of nutrient added to the loop, not by the addition of a base alone. As previously noted, some lines of mammalian cells are particularly sensitive to lactate, a cell metabolite which simply increases with passage of time between changes of liquid medium in accordance with the prior art mode of operation. Accordingly, it is desirable to provide a continuous monitor for the lactate and means for varying the delivery of the fresh solution feed pump responsive to changes in lactate level. The delivery rate for the fresh liquid medium must be sufficiently high to allow for withdrawal of a sufficient portion of the liquid within the loop to maintain lactate at a suitably low level. On the other hand, the conventional liquid medium for culturing mammalian cells represents a significant expense in the operation of the system of this invention, as well as in the prior art. Accordingly, it is desirable not to withdraw and add the liquid medium at a rate significantly higher than that required to maintain the waste metabolite content at a suitably low level. It has now been found that operation of the pump with a variation in delivery rate in response to the measured pH of the system enables the concentration of lactate to be maintained suitably below the maximum level for proper cell culturing, enables the concentration of nutrients to be maintained at a constant targeted level and, at the same time, minimizes consumption of the nutrient liquid medium consistent with the need for removal of toxic metabolites.

Accordingly, the system of the present invention includes a conventional tubular membrane cartridge and a circulating pump for circulating a nutrient-containing liquid medium through the tube side of the cartridge. The present invention also provides an oxygenator for oxygenating the liquid medium prior to entry into the cartridge. No stirred vessel is included at any point within the recirculating loop of liquid medium. A pH probe is provided in the loop along with means for regulating the output of a feed pump, responsive to the detected pH. Provision is also made for withdrawal of the liquid medium at a rate approximately equal to the rate of injection of fresh nutrient-containing solution with provision for maintaining the liquid medium at a suitable superatmospheric pressure to provide for a self-purging system. Operation at an elevated pressure, without a stirred vessel, has been found to be very effective in preventing contamination by undesired microorganisms.

The method of the present invention requires continuous pumping of the liquid within the recirculation loop, i.e. continuous circulation within an endless loop. Cells in a cell culture medium are placed in the cartridge on the shell side. The cartridge is mounted so that its longitudinal axis is oriented at an angle of 45°–90° with respect to the horizontal in order to maximize cell density and productivity. The recirculating liquid medium is oxygenated at some point upstream of the inlet of the cartridge. Fresh nutrient-containing liquid medium is continuously introduced into the loop, preferably upstream of the oxygenator and downstream of the circulating pump. Liquid medium exiting the bioreactor cartridge is split and a portion is continuously withdrawn from the loop at a point proximate the outlet of the bioreactor cartridge, at a rate equal to that of the feed of fresh nutrient-containing liquid. The pH within the loop is continuously measured, preferably at a point between the outlet of the bioreactor and the point of addition of fresh liquid medium. The feed pump for the fresh liquid medium is regulated responsive to the detected pH.

Other features and advantages of the present invention will become apparent to those skilled in the art from a reading of the description of the preferred embodiments which follows, in conjunction with the drawing.

BRIEF DESCRIPTION OF THE DRAWING

The sole drawing FIGURE is a flow chart showing the apparatus components of the system of the present invention.

DESCRIPTION OF THE PREFERRED EMBODIMENTS

A preferred embodiment of the present invention will now be described with reference to the drawing figure which shows various apparatus components of the present invention.

Indicated at 10 is a bioreactor which is preferably a "VITAFIBER" ® V Bioreactor. The "VITAFIBER" ® V Bioreactor is a cartridge containing a bundle of polysulfone hollow fibers providing approximately five square feet of semipermeable membrane surface and is commercially available through the AMICON Division of W.R. Grace & Co. The shell side of the bioreactor 10 is provided with a pair of vents, each closed by a three-way valve 13, which allow for introduction of the cells into the shell side of the bioreactor 10 and for the removal of same. The recirculation loop 20 is provided by proper connection of biocompatible tubing conventionally used in biochemical laboratories, e.g. polysilicone. The liquid nutrient-containing solution in loop 20 is split at a conventional laboratory tubing "T" 12 with a portion being continuously bled off through waste line 14 at a rate equal to the rate of injection of fresh liquid medium at "T" 18, another conventional laboratory tubing "T" connection. Pressure is maintained within the system within a range of 1–25 psig. The lower limit is dictated by the need to maintain a positive pressure, above atmospheric, within the system to prevent entry of foreign microorganisms. The upper limit is dictated only by the capacity of the apparatus. 25 psig is considered to be approximately the upper limit for the "VITAFIBER" ® V Bioreactor. Most preferably, the system is maintained at approximately 15 psig by a conventional duckbill check valve shown at 16.

Applicants have also discovered that the orientation of the longitudinal axis of the bioreactor, relative to the horizontal, is important with regard to both cell density and productivity of the desired metabolite, e.g. IgG. The present inventors have discovered that, in a horizontal hollow fiber bioreactor, the nature of convective flow within the reactor cartridge is such that large molecular weight growth stimulants, such as transferrin growth factors and albumin, are transported to the outlet end of the cartridge and accumulate there with a corresponding depletion at the inlet end. In other words, in a horizontally mounted bioreactor such high molecular weight growth stimulants will not perfuse evenly through the cell culture, with the cell culture adjacent the outlet end of the cartridge receiving the highest concentration of such nutrients. Applicants have demonstrated this experimentally by use of azo dye-labelled lactalbumin. They have also demonstrated experimentally that by orienting the longitudinal axis of the bioreactor at an angle of from 45° to 90° with respect to the horizontal the large molecular weight growth stimulants are much more evenly distributed throughout the cell culture. Specifically, they have found that at an angle of 60° or more with respect to the horizontal, the cell culture reaches maximum density and productivity in one-half the time required by an identical bioreactor arranged horizontally. Experiments indicate that little is to be gained by orientation at an angle beyond very slight advantage to be gained in terms of cell 60°. The very slight advantage to be gained in terms of cell density and productivity by raising the bioreactor to a vertical orientation is considered to be offset by manufacturing (packaging) problems which such a design would encounter.

Indicated at 21 is a pH probe which generates a signal, which signal governs operation of the fresh medium feed pump 22. The build up of toxic metabolites within the recirculating loop tends to lower pH, primarily due to the presence of lactate which is a metabolite of the mammalian cell. On the other hand, the conventional nutrient medium containing glucose, vitamins and amino acids is slightly basic, e.g. pH 7.3 or 7.4. Thus, the delivery of the fresh medium, at a constant pH, by pump 22 is regulated responsive to the signal from the pH probe 21 to maintain a pH at a particular level selected as optimum for the particular cell line being cultured. In this manner the nutrient level is maintained at a constant level within the recirculation loop, in contrast to mere pH control as in the "VITAFIBER ® II/Plus" system. The selected pH for the recirculation loop will typically range between 6.5 and 7.5 and, for the production of IgG from hybridoma cells, will preferably be about 6.8. Because lactate level is precisely controlled responsive to pH in the system of the present invention, there is no need for a pH color indicator in the liquid medium, as required by the prior art. However, such a color indicator may be optionally added if desired.

Fresh nutrient-containing liquid medium is continuously added to the loop by a peristaltic pump 22 through "T" 18 at a point downstream of the pH probe 21. Continuous circulation within loop 20 is provided by a gear pump 24.

Downstream of the recirculating pump 24 is provided an oxygenator 26. As oxygenator 26 applicants have employed 0.132" ID and 0.183 OD silicone tubing mounted within a 2" I.D. polysulfone tube. Air is pumped by an air pump 28 into the shell side of oxygenator 26 with the liquid medium passing through the tubes of the oxygenator. The partial pressure of oxygen within in the circulating liquid medium within loop 20 is preferably maintained at 100-150 mmHg. In actual practice, applicants have been successful in maintaining a partial pressure of oxygen of enhanced controlability is particularly important in the about 138 mmHg. The air pump 28 is a conventional, commercially available diaphram pump.

Upon exiting oxygenator 26 the circulating liquid medium passes through a 5 micron filter 30 such as the polypropylene membrane filter marketed by Pall Biomedical Products Corporation.

Indicated at 32 is an incubator oven which contains the bioreactor 10, the pH probe 21, the oxygenator 26 and the filter 30. The interior of the oven is maintained at a temperature optimum for the particular cell strain being cultivated and will typically be about 37° C.

The apparatus and method of the present invention will find use in many different medical and biochemical applications. For example, the disclosed apparatus and method have proven to be particularly useful for the production of immunoglobulins such as IgG from hybridoma cell lines. The system and method can also be used to culture any other cell line which has been successfully cultured in hollow fiber systems such as animal embryo tissues, human lung tissue and various human and animal carcinomas.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A method of culturing cells comprising:
   placing cells within the shell side of a hollow fiber membrane cartridge, said cartridge having an inlet end and an outlet end, said cartridge being oriented with its longitudinal axis at 45°-60° with respect to the horizontal, said outlet end being raised above the inlet end; and
   continuously circulating a liquid medium containing nutrients through the tube side of said cartridge.

2. A method of culturing cells, said method comprising:
   continuously circulating, with a pump, a liquid medium containing nutrients for the cells through an endless loop closed to the ambient atmosphere, said loop including semipermeable membrane tubes of a tubular membrane cartridge, said tubes extending between a fluid input end and a fluid output end, the cells to be cultured being contained within the shell side of said cartridge, wherein said output end is raised above said input end;
   oxygenating said liquid medium in said loop;
   continuously measuring the pH of the liquid medium in the loop and generating a signal representative of the pH;
   continuously adding fresh nutrient-containing liquid medium at a constant pH to said loop in an amount varied in accordance with the measured pH; and
   continuously removing said amount of liquid medium from the loop.

3. The method of claim 2 wherein pH is controlled by said adding within a pH range of 6.5-7.5.

4. The method of claim 2 wherein the pressure within the loop is maintained at 1-25 psig.

5. The method of claim 2 wherein the partial pressure of oxygen dissolved in the liquid medium entering the cartridge is 100-150 mmHg.

6. The method of claim 2 wherein said tubular membrane cartridge is arrange with its longitudinal axis 45°-90° to the horizontal.

7. The method of claim 2 wherein said tubular membrane cartridge is arranged with its longitudinal axis at an angle of 45°-90° to the horizontal.

8. The method of claim 2 wherein the point of removal of the liquid medium from said loop is between the output end of the cartridge and the pump and the point of addition of fresh medium is between the point of removal and the pump.

9. The method of claim 8 wherein the pH is measured at a point in the loop between the point of removal and the point of addition.

10. A cell culturing system comprising:
    a tubular membrane cartridge having a shell and a plurality of tubular semipermeable membranes mounted within said shell and extending between a fluid input end and a fluid output end, wherein said output end is raised above said input end, said tubular membranes serving to divide the interior of said shell into an intratubular space and an extratubular space, said shell having first and second spaced-apart ports communicating with the extratubular space for introduction and removal of the cells and cell products;
    a circulating pump for circulating a nutrient-containing liquid medium through said tubular membranes;
    an oxygenator for oxygenating said liquid medium;
    an endless circulation loop, closed to the ambient atmosphere and communicating with said fluid input end and said fluid output end, said loop including said circulating pump and said oxygenator, but no stirred vessel;
    a variable delivery feed pump for continuously injecting fresh nutrient-containing solution into said loop;
    a pH probe in said loop and means for regulating the output of said feed pump responsive to changes in the pH as determined by said probe; and 11. The system of claim 10 wherein the point of withdrawal of said liquid medium is between the output end of the cartridge and the circulation pump and wherein the point of injection of the fresh nutrient-containing liquid medium is between said point of withdrawal and said circulating pump.

12. The system of claim 10 wherein said forging means comprises a check value.

13. The system of claim 10 wherein said loop further includes a filter for removal of solids.

14. The system of claim 10 further comprising an incubator cabinet having an interior containing said cartridge and said oxygenator and means for maintaining the interior of said cabinet at a temperature above room temperature and suitable for culturing the cells.

15. The system of claim 10 wherein said cartridge is oriented with its longitudinal axis at an angle of 45°-90° with respect to the horizontal.

16. The system of claim 15 wherein said cartridge is oriented with its longitudinal axis at an angle of 45°-60° with respect to the horizontal.

* * * * *